United States Patent [19]
Netzer

[11] Patent Number: 5,682,788
[45] Date of Patent: Nov. 4, 1997

[54] DIFFERENTIAL WINDSHIELD CAPACITIVE MOISTURE SENSOR

[76] Inventor: Yishay Netzer, Yuvalim, Doar Na Misgav, Israel

[21] Appl. No.: 501,684

[22] Filed: Jul. 12, 1995

[51] Int. Cl.$^6$ .................... G01N 5/02; H02P 1/04
[52] U.S. Cl. .................... 73/73; 324/687; 324/661; 318/444; 73/29.01
[58] Field of Search .................... 324/61, 687, 688, 324/663–665, 690; 318/444; 73/73, 29.01

[56] References Cited

U.S. PATENT DOCUMENTS

| | | | |
|---|---|---|---|
| 2,718,620 | 9/1955 | Howe | 324/61 |
| 3,493,854 | 2/1970 | Zurbrick | 324/61 |
| 3,515,987 | 6/1970 | Zurbrick et al. | 324/61 |
| 3,671,857 | 6/1972 | Bergmanis et al. | 324/61 QS |
| 3,694,742 | 9/1972 | Bergmanis et al. | 324/61 QS |
| 3,774,237 | 11/1973 | Hardway, Jr. | 324/61 R |
| 3,774,238 | 11/1973 | Hardway, Jr. | 340/258 C |
| 3,811,087 | 5/1974 | Schmelzer | 324/58.5 A |
| 3,826,979 | 7/1974 | Steinmann | 324/61 R |
| 3,902,040 | 8/1975 | Ikeda et al. | 219/203 |
| 4,016,490 | 4/1977 | Weckenmann et al. | 324/61 R |
| 4,208,909 | 6/1980 | Maltby et al. | 73/304 |
| 4,542,325 | 9/1985 | Kobayashi et al. | 318/483 |
| 4,554,493 | 11/1985 | Armstrong | |
| 4,567,412 | 1/1986 | Graham | 318/483 |
| 4,568,874 | 2/1986 | Kramer et al. | 324/61 R |
| 4,613,802 | 9/1986 | Kraus et al. | |
| 4,703,237 | 10/1987 | Hochstein | |
| 4,752,855 | 6/1988 | Fedter et al. | 361/286 |
| 4,757,252 | 7/1988 | Maltby et al. | 324/61 P |
| 4,805,070 | 2/1989 | Koonts et al. | |
| 4,827,198 | 5/1989 | Mueller et al. | |
| 4,831,493 | 5/1989 | Wilson et al. | |
| 4,859,867 | 8/1989 | Larson et al. | |
| 4,987,354 | 1/1991 | Steinmann | 318/444 |
| 4,992,741 | 2/1991 | Douglas et al. | 324/671 |
| 5,223,796 | 6/1993 | Waldman et al. | 324/687 |
| 5,402,075 | 3/1995 | Lu et al. | 324/664 |

*Primary Examiner*—Hezron E. Williams
*Assistant Examiner*—Jay L. Politzer
*Attorney, Agent, or Firm*—Mark M. Friedman

[57] ABSTRACT

A differential capacitive moisture sensor, relying for its operation on the time-varying couplings in two moisture-sensing regions to provide indication of presence of moisture, with selectivity of sensing surface provided by a shielding electrode, and with temperature information provided by a simultaneously-fabricated resistive temperature sensor. Various electrode connections and sensor electronics may be used.

40 Claims, 13 Drawing Sheets

DIFFERENTIAL WINDSHIELD CAPACITIVE MOISTURE SENSOR

FIELD AND BACKGROUND OF THE INVENTION

The present invention relates to a moisture sensor and, more particularly to a moisture sensor especially suitable for use in the sensing of moisture on an automobile windshield. This device operates on a differential capacitive moisture detection principle, which has been discovered by the inventor, and will be described below, which results in a sensor with greater sensitivity, and additionally, with directionality, the ability to selectively sense moisture on either surface of the windshield, a feature not found in the prior art. Prior Art automotive windshield moisture sensors are either bulky, conspicuous, expensive, electro-optical moisture sensors, of limited sensing area, simultaneously expensive, and having mounting position limitations; or, capacitive moisture sensors, which are unable to distinguish between a moisture signal and normally-encountered background reference signal variations due to stress and temperature variations in the dimensions of the windshield.

Various attempts have been made to solve the specific problems of the electro-optical moisture sensors, as mentioned above. These have been in the category of single-ended capacitive moisture sensors, which operate by providing changes in electrical capacitance between two sensing electrodes, in response to presence of moisture on a surface in the region between the electrodes. These have the aforementioned difficulty of distinguishing between baseline signal and moisture signal, as mentioned above, due to the large "dry-" condition background baseline signal, and small change to this signal level due to presence of rain. Therefore, variations of output which indicate rain are comparable to normally-encountered changes in baseline reference signal, giving false indications, and non-indications, concerning presence of moisture. A further disadvantage of prior-art capacitive moisture sensors is the inability to distinguish between moisture on the outside versus on the inside of the windshield, making it difficult to use as a wiper controller or as a defogger or as a defroster sensor. For these reasons, the capacitive moisture sensors are not practical, and do not appear to be presently in wide use in the automotive marketplace.

In more detail, in the prior art, electro-optical moisture sensors are the most common and are used for detection of raindrops by sensing of change in the total internal reflection of light beams off the front windshield glass-air interface. A typical sensor of this type is described in U.S. Pat. No. 4,859,867. Electro-optical moisture sensors suffer from several disadvantages:

They are conspicuously mounted on the internal side of the windshield.

The proper operation is critically dependent on the mechanical stability of the mounting.

They are often sensitive to extraneous light.

They are relatively expensive.

An alternative method of sensing moisture on the windshield surface relies on the relatively large dielectric constant electrodes of water (approximately 80) as it affects the capacitance between a set of conductive transparent electrodes deposited on the windshield. Sensors based on this method are integral with the windshield and are potentially less expensive and non-conspicuous. Two such sensors are described in U.S. Pat. Nos. 4,805,070 and 4,831,493. In these patents, a conductive coating is applied on the outside surface of the windshield. Its disadvantage is exposure to abrasion due to the combined effects of wiper motion and airborne particles. Another approach is to deposit the conductive electrodes on the inside of the front laminate of the "sandwich" windshield glass for protection of the conductive coating. Typical moisture sensors of this type are described in U.S. Pat. No. 4,703,237; in U.S. Pat. No. 4,827,198; in U.S. Pat. No. 4,613,802; and in U.S. Pat. No. 4,554,493; where the capacitive effect of water drops changes the resonant frequency of a resonant circuit. In all prior art capacitive moisture sensors in which the dielectric glass layer separates the capacitor plates from the water-droplets-sensitive surface, the relative change of the capacitance due to water drops is very small. The capacitive moisture sensor described in U.S. Pat. No. 3,826,979 aims to diminish the fixed constituent of the capacitance (in the dry condition) by shielding part of the parasitic capacitive coupling, thereby reducing the dry reference background signal level. The improvement, however, is only partial since the residual "dry" capacitance is still significant relative to the moisture induced capacitance increase. A further difficulty is that the "dry" capacitance itself is not stable, in particular as a result of distortion in the internal plastic layer—that result from windshield dimensional changes due to temperature and mechanically induced stress. As a result, the signal due to surface moisture is virtually indistinguishable from the error signal due to capacitance changes. The reliability of this kind of capacitive windshield moisture sensors is therefore poor.

An additional shortcoming of prior art capacitive moisture sensors is their non-directionality, i.e., their sensitivity to moisture on both surfaces of the windshield, i.e., they do not distinguish between moisture on the external surface of the windshield and condensation on the internal side. Similarly, they are sensitive to adjacent objects in the inside of the car, such as when the driver manually wipes off condensation accumulated on the internal surface.

Thus, in general, capacitive windshield moisture sensors suffer from both lack of sensitivity and stability on the one hand, and from non-directionality on the other hand. For this reason only electro-optical windshield rain sensors have had any commercial success.

There is thus a widely recognized need for, and it would be highly advantageous to have, an improved moisture sensor, suitable for automotive windshield application, which is inexpensive, sensitive, stable with time and temperature, does not obstruct the driver's view so it is flexible with respect to mounting position, and is "directional", i.e., it is selectively sensitive to moisture on only one side of the windshield.

SUMMARY OF THE INVENTION

According to the present invention there is provided an automotive windshield moisture sensor.

According to further features in preferred embodiments of the invention described below, there is provided a directional windshield moisture sensor.

According to another embodiment, there is provided a pair of directional moisture sensors, integrally manufactured in the windshield structure.

According to another embodiment, there is provided an additional temperature sensor element, which, in conjunction with the moisture sensor, provides the capability to differentiate snow or ice from rain or "fogging" condensation such as often found on the inside of the windshield.

According to another embodiment, the moisture detector is simultaneously, integrally, manufactured in the windshield with an electrical heating layer in the windshield.

According to another embodiment there is provided an independent moisture detector, which can be separately manufactured, and which is suitable for mounting on a conventional windshield.

The present invention successfully addresses the shortcomings of the presently known configurations by providing capacitive moisture sensor.

The present invention discloses a novel, directional, differential, capacitive moisture sensor, which solves the problems of automotive windshield moisture-sensing.

More specifically, the directional, differential, capacitive moisture sensor of the present invention, is inexpensive, does not obstruct the drivers view, can be placed in the wiping area, is not subject to aging due to abrasion, is sensitive, and stable with time and with stress and temperature effects on windshield dimensions, is sensitive to moisture on only one surface of the windshield, hence insensitive to moisture and conductive objects on or near the opposite surface of the windshield. Also, this moisture sensor is capable of sensing moisture over a large surface area, unlike the electro-optical moisture detectors, which are focussed to sample moisture only in a small region.

One "unit" of the moisture sensor of the invention may be "mounted", either as a separately manufactured add-on device, or integrally manufactured, in a windshield, for the purpose of rain-sensing, by monitoring moisture on the outer surface of the windshield. Incorporating a temperature-sensor, as mentioned above, then gives the capability to differentiate between non-freezing rain, and freezing precipitation, snow, slush, ice, freezing rain, necessitating windshield heating, as well as wiping. A second unit may be "mounted" in the opposite orientation, to control a blower or blower-plus-heater, to "defog" or "defrost" the inner windshield surface, again, preferably in conjunction with a temperature sensor to control the temperature of the air source provided to the blower, as appropriate to the moisture to be dissipated. A pair of moisture sensors may be integrally manufactured with the windshield, temperature-sensor, and heating element; or add-on unit may be provided in existing cars as an after-market product.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a directional, differential, capacitive moisture sensor, which can be integrally manufactured in an automotive windshield, or as an add-on device.

Specifically, the present invention can be used to sense presence of various types of moisture on a windshield, and to differentiate between them, sufficiently well to control wipers, heater and blower, for wiping, deicing, defogging and defrosting, to restore, or maintain the drivers visibility.

The principles and operation of a directional, differential, capacitive, moisture sensor according to the present invention may be better understood with reference to the drawings and the accompanying description.

Figure 1A:
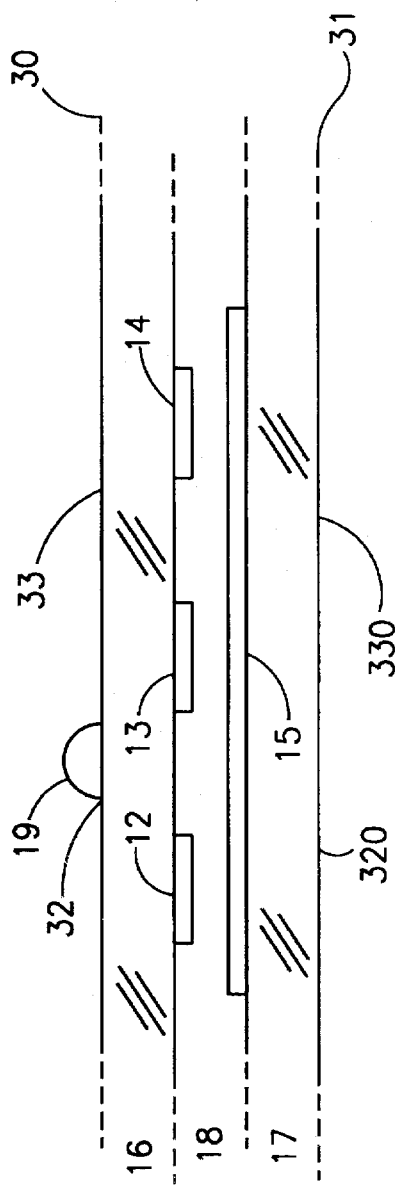
FIG. 1A is a directional, differential, capacitive moisture sensor.

Referring now to the drawings, FIG. 1A illustrates the simplest "unit" directional, differential, capacitive, moisture sensor.

The embodiment in FIG. 1A illustrates the moisture sensor as integrally manufactured in an automotive windshield. The windshield consists of laminated "sandwich glass", two glass laminated layers, 16 and 17, separated by a layer of plastic laminate, 18, with electrodes 12, 13, 14, deposited on the lower surface of glass laminate layer, 16; and electrode, 15, deposited on the upper surface of glass layer, 17. This construction results in a structure such that electrodes on any surface are substantially co-planar with each other, and parallel to all the surfaces of the glass laminates. For discussion purposes, we will consider the layer, 16, to be the outer layer, and layer 17, to be the inner layer, and we will discuss the effects of moisture on the outer glass laminate surface, 30, and on the inner glass laminate surface, 31. The simplest "unit" moisture sensor of the invention consists of three "active", i.e., non-grounded, electrodes, as will now be described. It is worthwhile to note that the three-electrode Capacitive Detector Device of U.S. Pat. No. 3,826,979, is not in the category of our invention, since its center plate is grounded.

A basic capacitive moisture sensor exhibits capacitance change due to moisture in the sensing area, such as water drop, 19, in sensing area 32 of FIG. 1A. Since water has a dielectric constant of about 80, compared with that of air of about 1, and capacitance of a capacitor is proportional to the dielectric constant of the dielectric between its plates, we see that an increase in moisture in the sensing areas, 32, and 33, between electrode pairs, 12 and 13, and 13 and 14, respectively, will result in an increase in capacitance between the corresponding electrode pairs. If there is uniform increase of moisture in the sensing areas 32 and 33, then the two capacitances will increase equally. If, as in FIG. 1B, balanced, equal frequency and amplitude, 180 degree out-of-phase excitations are applied to the electrodes, 12 and 14, and the spacings are equal, and the sandwich-glass is uniform, then, when both the sensing areas 32 and 33 on surface 30, are dry or uniformly moist, the capacitively coupled signal voltage at electrode 13 due to each, will be identical, and the total will be substantially zero, due to equal coupling, through equal capacitances, independent of the exact capacitance value.

The invention depends on the inventor's realization, that the moisture in the two sensing areas 32 and 33, in general, at any instant of time is not equal, even though the average of the moisture in the two areas over a long period of time may be expected to be equal. Hence, at any given instant, there is an asymmetry in the moisture in the two sensing areas, a corresponding instantaneous capacitance imbalance, a corresponding imbalance of the signal couplings to electrode 13, and a resulting finite, non-zero, detectable, imbalance signal at electrode 13, to indicate presence of moisture. The polarity of the imbalance signal is not known, since which side has greater moisture at any given instant is not known. This is, however, a practical moisture detector, since in the sensing electronics, it is possible to incorporate "absolute-value" circuitry, which then detects imbalance of either polarity.

Because this is a differential sensor, it is substantially insensitive to dimensional changes in the substrate, the laminated windshield sandwich glass, in this example. A stress-induced or temperature induced expansion or contraction is expected to affect the dimensions, especially thickness, of both sensing areas substantially equally, resulting in substantially no false indication of moisture. This feature is due to the differential nature of the sensor, and the substantially uniform dimensional change in the sensing area, and is its first advantage over the prior-art single-ended, non-differential, capacitive moisture sensors.

Further, the differential capacitive moisture sensor is more sensitive to moisture in a practical circuit application than the prior-art single-ended sensors. The single-ended sensors operate with non-zero reference "dry" signal output. Changes in this reference signal must be detected to detect presence of moisture. These changes are small, and the changes due to substrate dimensional changes are of comparable amplitude to the moisture signals, so the prior-art single-ended moisture sensors are not practical. The differential moisture sensor on the other hand has a reference signal of substantially zero, so the moisture signal is immediately large, and easily detected; and the substrate dimensional changes are balanced out, due to sensor symmetry, so there is no error signal due to substrate dimensional changes. For these reasons, the net result is that the differential moisture sensor is much more sensitive than the prior-art single-ended sensors.

Directionality, i.e., sensitivity to moisture on only one surface of the substrate, is provided by the shield electrode, 15, in FIG. 1A. This shield electrode is connected to the electronics system ground, providing electrical isolation of electrode pairs, 12 and 13, and 13 and 14, from regions, 320 and 330, respectively, on surface 31, which would otherwise have also been sensing areas similarly to areas, 32 and 33, respectively, on surface 30. Thus, directionality, sensitivity to moisture on only one surface of the substrate, is provided, as is desirable in the automotive windshield application, as in many other applications for sensors in general.

The flexibility of mounting of the windshield moisture detector is provided by implementing the electrodes as, for example, a vacuum-deposited thin film coating of a transparent, electrically-conductive, material, such as Indium-Tin-Oxide, such as has been used for electrical windshield heating. Using such a transparent material, makes it possible to locate the moisture sensor in the wiping area of the windshield. This is desirable, since wiping will remove the moisture rapidly from the sensed area of the windshield, resulting in de-activation of the wipers promptly upon cessation of rainfall, for example.

When the moisture sensor is used to detect moisture in the form of condensation on the inside of the windshield, the flexibility of mounting is also important, since the automobile designer will want to locate the moisture detector in a position such that after the "defogging" for example, is complete, the blower and heater would be turned off. This depends on the knowledge of the automobile designer of the air flow in the car. It is important to note that this directional, differential, capacitive, windshield, moisture sensor, now makes practical moisture detection on the inside surface of the windshield. Previously, it would have been necessary to mount an electro-optical moisture sensor on the outside of the windshield, to focus it on the inner surface of the windshield.

Figure 4:
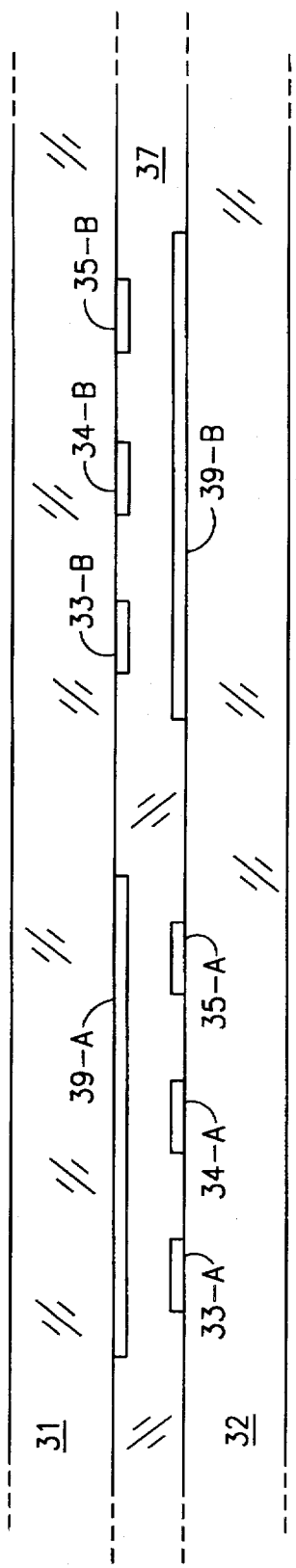
FIG. 4 is a pair of sensors as in FIG. 1A, shown mounted for sensing two surfaces of the windshield.
Figure 4A:
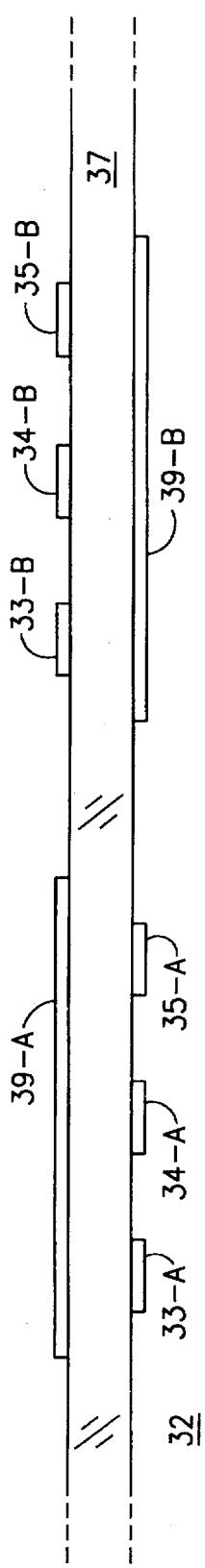
FIG. 4A is a pair of standalone sensors.

A pair of moisture sensors of the invention are shown in FIG. 4, illustrating the fabrication, to result in one sensor each for moisture on outer and inner windshield surfaces.

Figure 5:
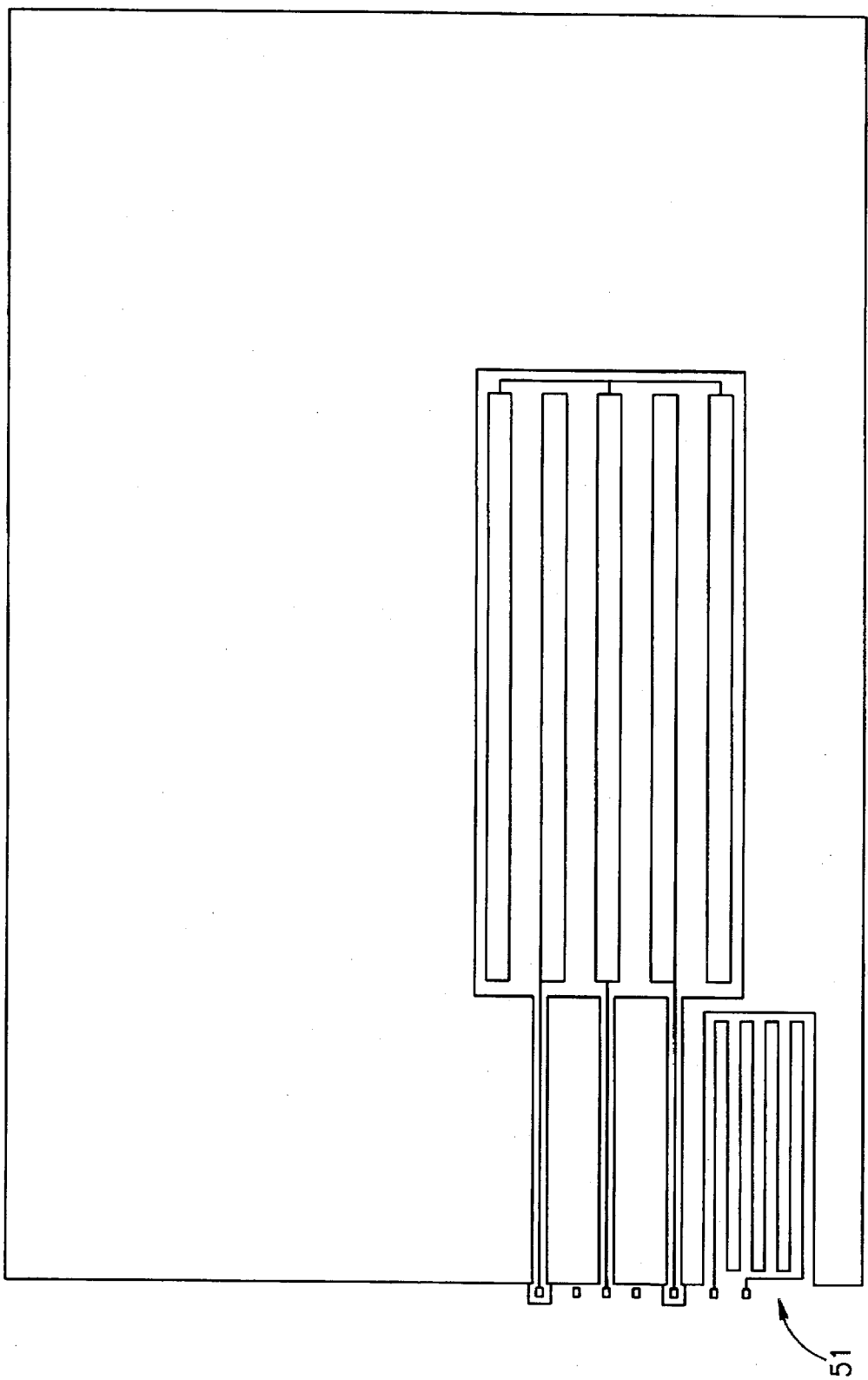
FIG. 5 is an example electrode pattern, incorporating a temperature-sensing element.

As mentioned previously, an accompanying temperature sensor may be implemented with the same vacuum-deposited thin film which is used to fabricate the moisture sensor electrodes. This is conveniently done by depositing as a temperature sensing element, a long, thin, pattern, for example, in the shape of a "snake", element 51, as shown in FIG. 5, accompanying an alternative electrode configuration, which has been built. The resistance of this element as a function of temperature is then monitored.

Figure 1C:
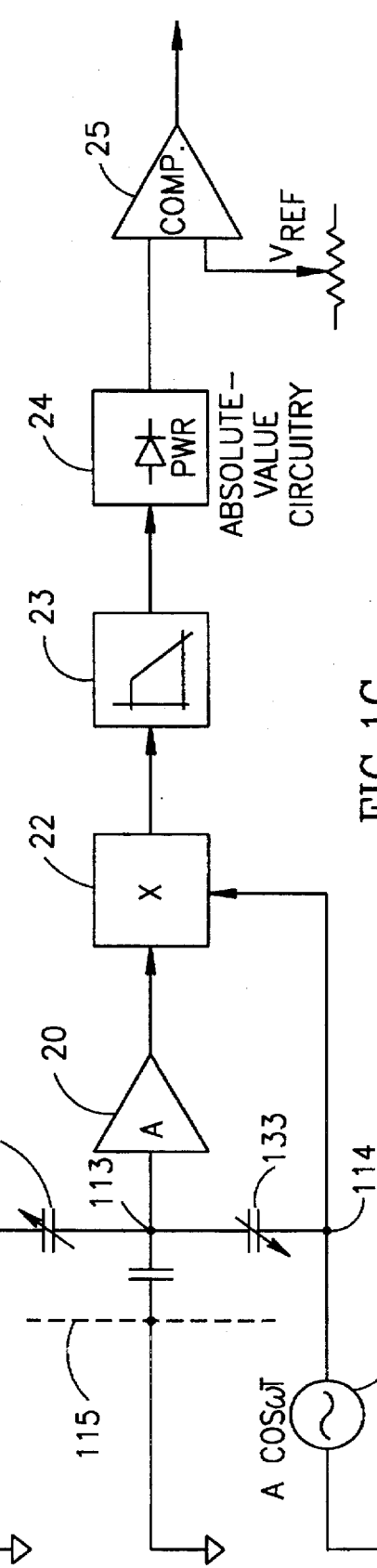
FIG. 1C is a schematic representation of the sensor of FIG. 1A, 1B.
Figure 1B:
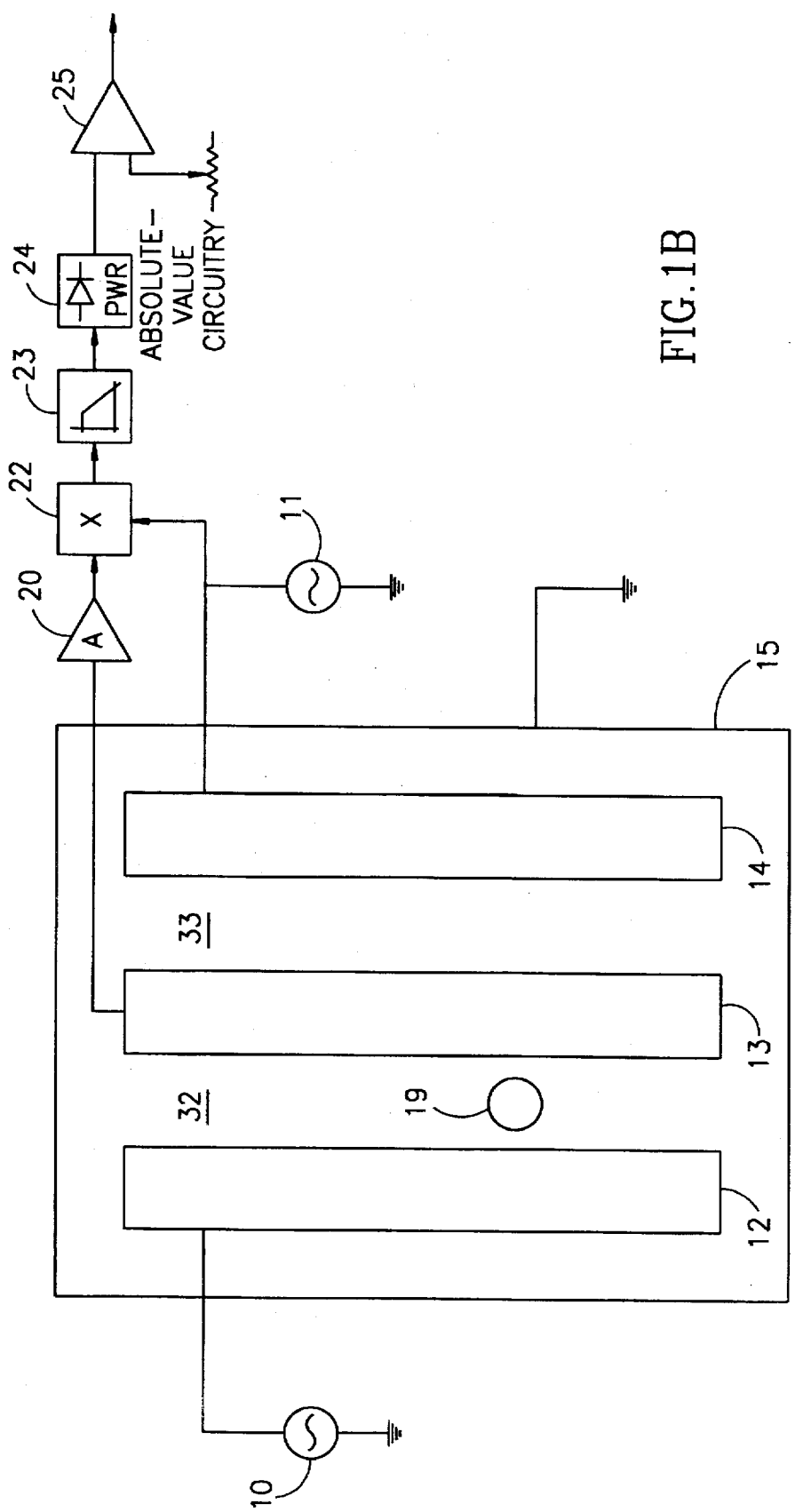
FIG. 1B is the directional, differential, capacitive moisture sensor of FIG. 1A, with one possible configuration of excitation and sensing electronics.

The electronics for the differential sensor of FIG. 1A are shown in FIG. 1B. An electrical schematic representation of the sensor is also shown in FIG. 1C. This is a representative implementation, which is not the only possibility, as will be discussed. This system includes the previously-discussed 180-degree out-of-phase excitation sources, 10 and 11, driving electrodes 12 and 14, which bracket sensing electrode, 13, and are equidistant from it, providing a net "dry"-condition zero-valued reference signal at electrode 13. The return for the sources, and the reference voltage for measuring the output at electrode, 13, is the system "ground". The shield electrode, 15, when included, and used with the circuitry shown here, is also connected to the system ground. Signal appearing at electrode, 13, in case of asymmetry of moisture in sensing regions, 32 and 33, which is represented by "raindrop", 19, is amplified, here, in single-ended inverting, transimpedance, "charge", amplifier, 20, synchronously-demodulated by multiplication in multiplier, 22, with the output of one of the excitation sources, here, 11, The output of the multiplier is low-pass-filtered in low-pass-filter block, 23, to remove the excitation-frequency carrier. The resulting low-pass-filtered, time-varying, "dc" level is then "full-wave-rectified" in an absolute-value amplifier circuit, 24, before being applied to voltage-comparator with moisture detection level input, 25. This detection electronics provides good immunity to non-signal, carrier frequency, interference, is relatively simple, and inexpensive, has been used with the moisture sensor of the invention, but other designs may also be used. Further, the electronics may change configuration, to suit changes in the electrode configuration, or connections to the electrodes, due to interchanging their functions. It is worthwhile to mention that a charge amplifier is a specific type of transimpedance amplifier, in which the feedback element is ideally a pure capacitance, so that with a pure capacitive source impedance, the voltage gain is given by the ratio of feedback to signal source internal capacitor, and inverted.

Figure 2A:
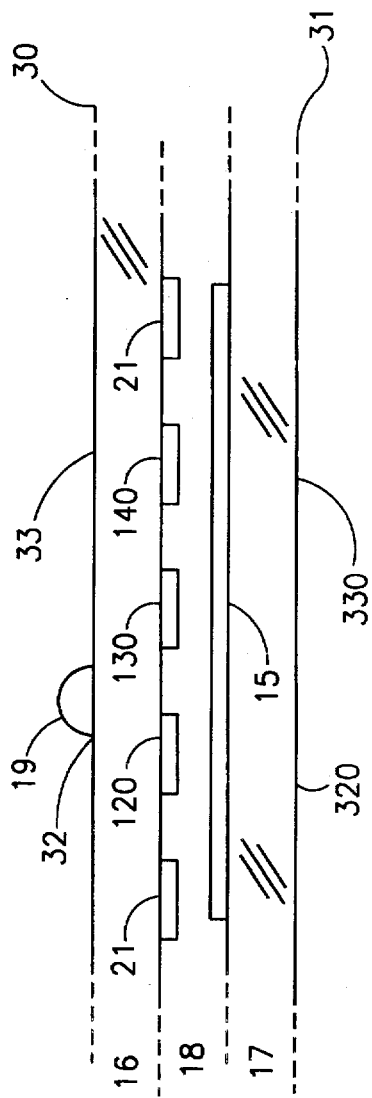
FIG. 2A is a modified, directional, differential, capacitive, moisture sensor.
Figure 2C:
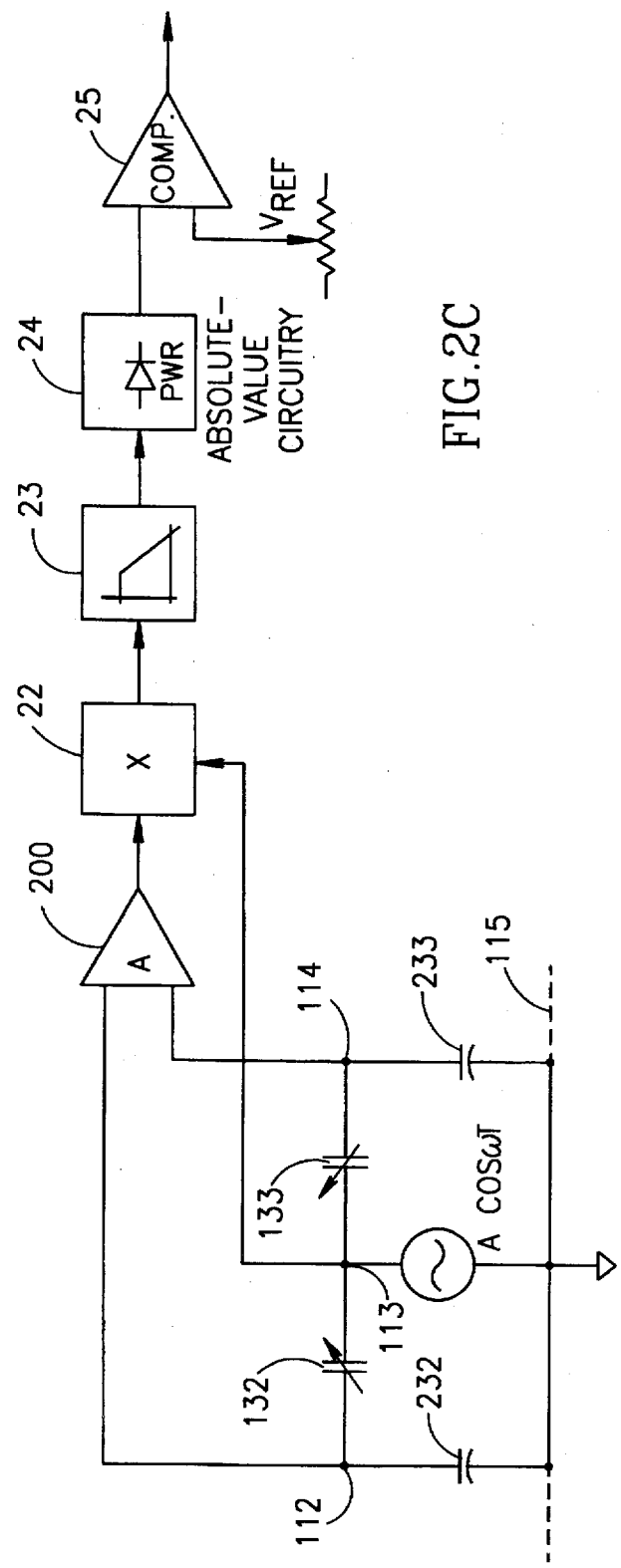
FIG. 2C is a schematic representation of the sensor of FIG. 2A, 2B.
Figure 2B:
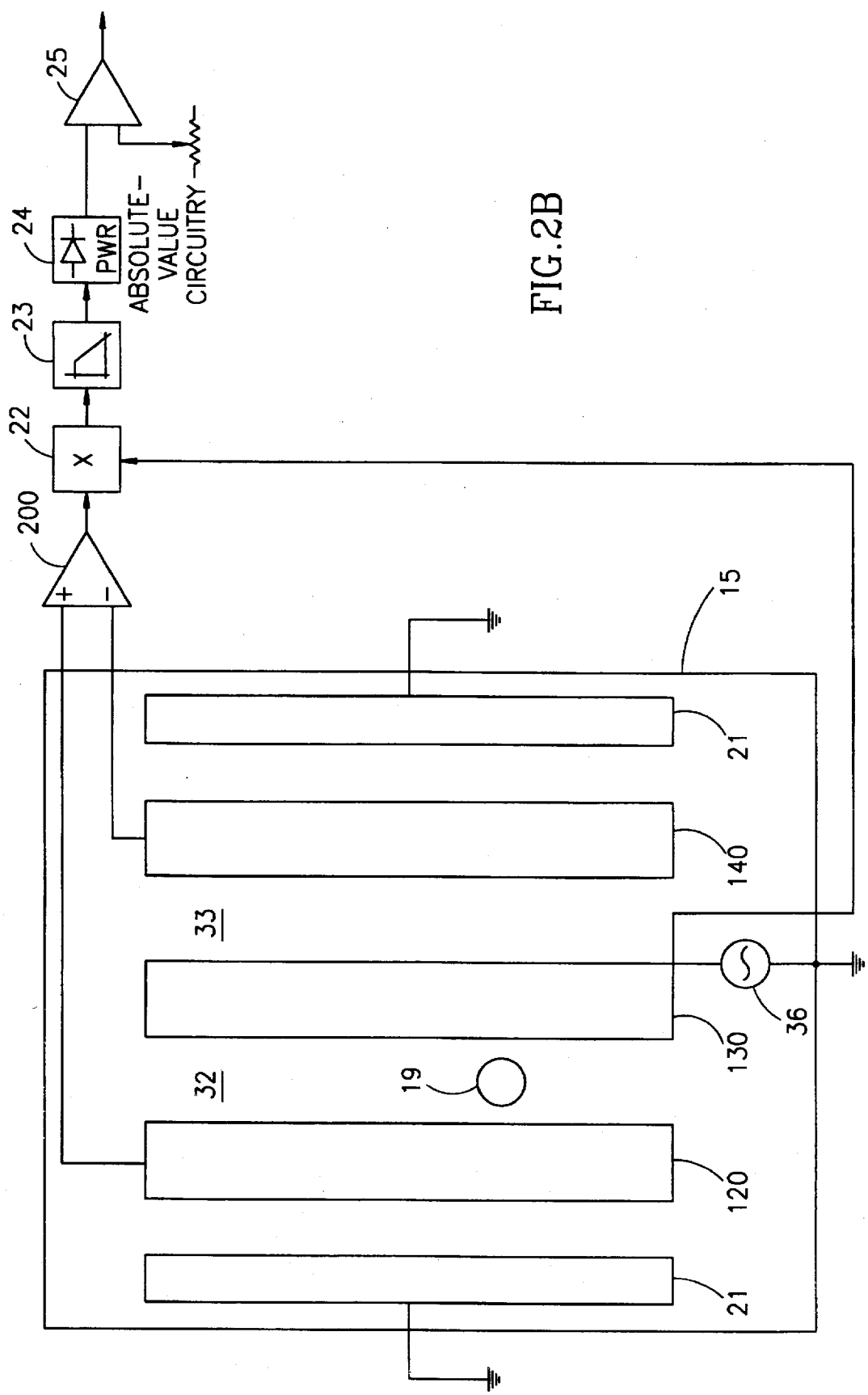
FIG. 2B is the modified, directional, differential, capacitive moisture sensor of FIG. 2A, with alternative configuration of excitation and sensing electronics.

Another possible configuration is shown in FIGS. 2A and 2B, and represented schematically in FIG. 2C. Elements of FIGS. 2A and 2B which have similar functionality to those of FIG. 1A and 1B, are numbered similarly. The function of electrode, 13, in FIG. 1A and 1B was as a single sensing electrode, with two excitation electrodes, 12 and 14. Here, 130 is a single excitation electrode, and electrodes 120 and 140, are a "true-differential" output-electrode pair. Here, the sensor must incorporate the shield, ground-plane, electrode, 15, which provides the directional properties of the sensor, since this serves as the return electrode for the excitation. This sensor now functions as a bridge, with four capacitance legs. The two sensing capacitances are between the active electrode pairs, 130 and 120, and 130 and 140, corresponding to sensing areas 32 and 33, respectively, as before. However, the capacitance from sense electrode, 120, to ground plane, 15, and the capacitance from sense electrode, 140, to ground plane, 15, provide the two reference capacitors for the bridge. These two capacitances depend on the plastic laminate as their dielectric. The single-ended-input, transimpedance, charge, amplifier, 20, of FIG. 1B has been replaced with the differential-input voltage amplifier, 200, of FIG. 2B. This may be realized as an instrumentation amplifier, as is well-known. The rest of the "receiver" electronics is the same. Also, two grounded "guard" electrodes, 21, have been added outside sense electrodes, 120 and 140, to shield them from the bottom of the substrate, in case the electrode, 15, does not extend far beyond the outer edges of sense electrodes 12 and 14. Alternatively, these guard electrodes may be bootstrapped with buffer amplifier to their adjacent sense electrodes. The single excitation source, 36, also provides the multiplier/demodulator reference input signal. The functionality of the sensor moisture sensor is the same as before, but the signal output is different, since the electrodes functionality is interchanged, necessitating a change in the sensor electronics. One possible advantage of this arrangement over that in FIGS. 1A and 1B, is that the differential-input amplifier, 200, may be less sensitive to radio-frequency interference (RFI) than the single-ended-input amplifier, 20. A further possible advantage of this arrangement over that of FIGS. 1A, 1B may occur in case of very large moisture signal. There may be some condition in which it is desired to add the signal at electrodes 120 and 140, in additional circuitry to provide an additional non-differential magnitude indication.

Figure 1D:
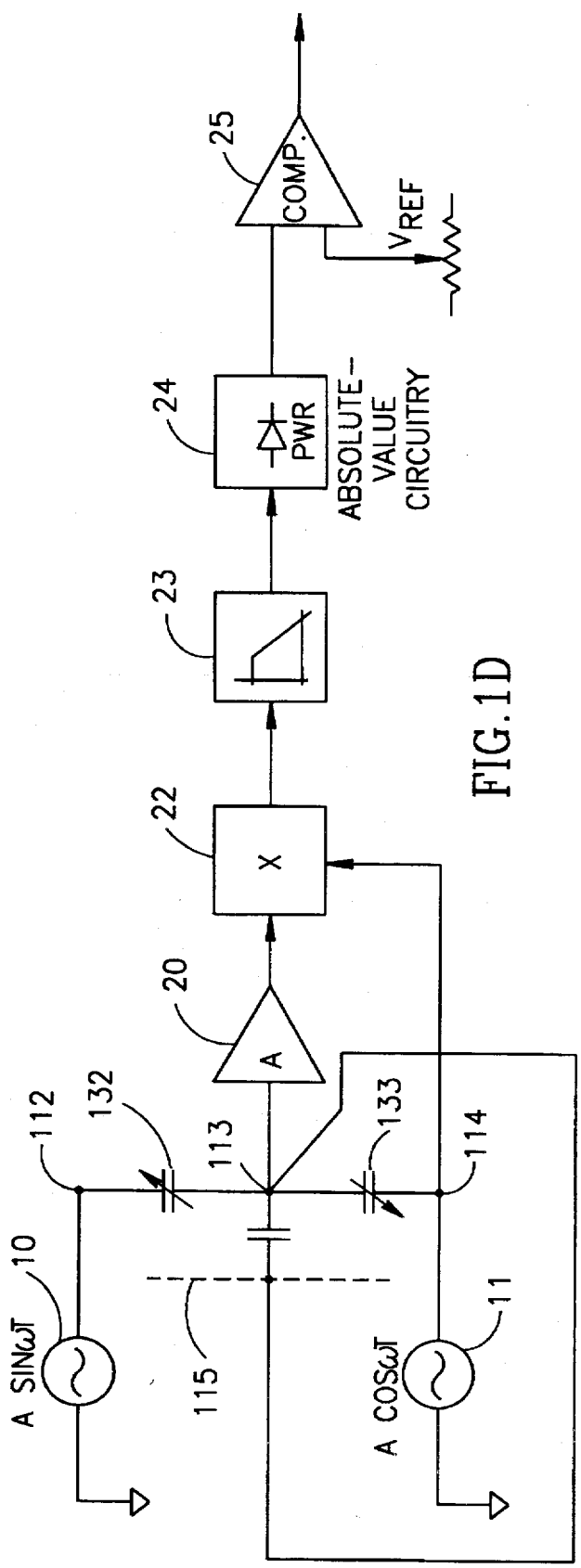
FIG. 1D is a schematic representation of the sensor of FIG. 1A, 1B.
Figure 1E:
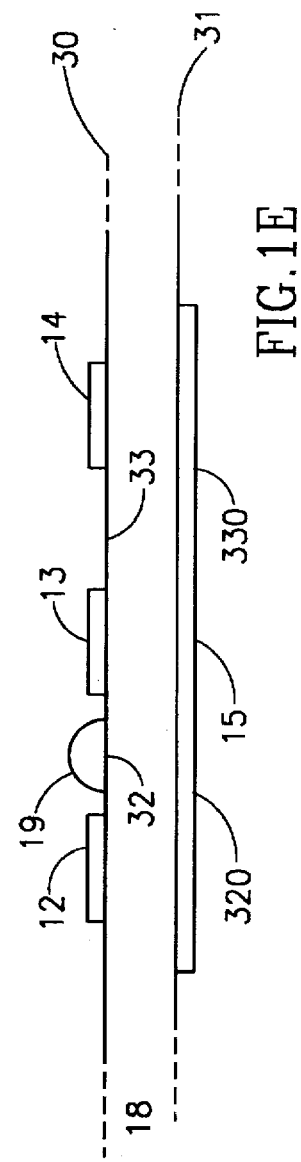
FIG. 1E is a standalone sensor.
Figure 3A:
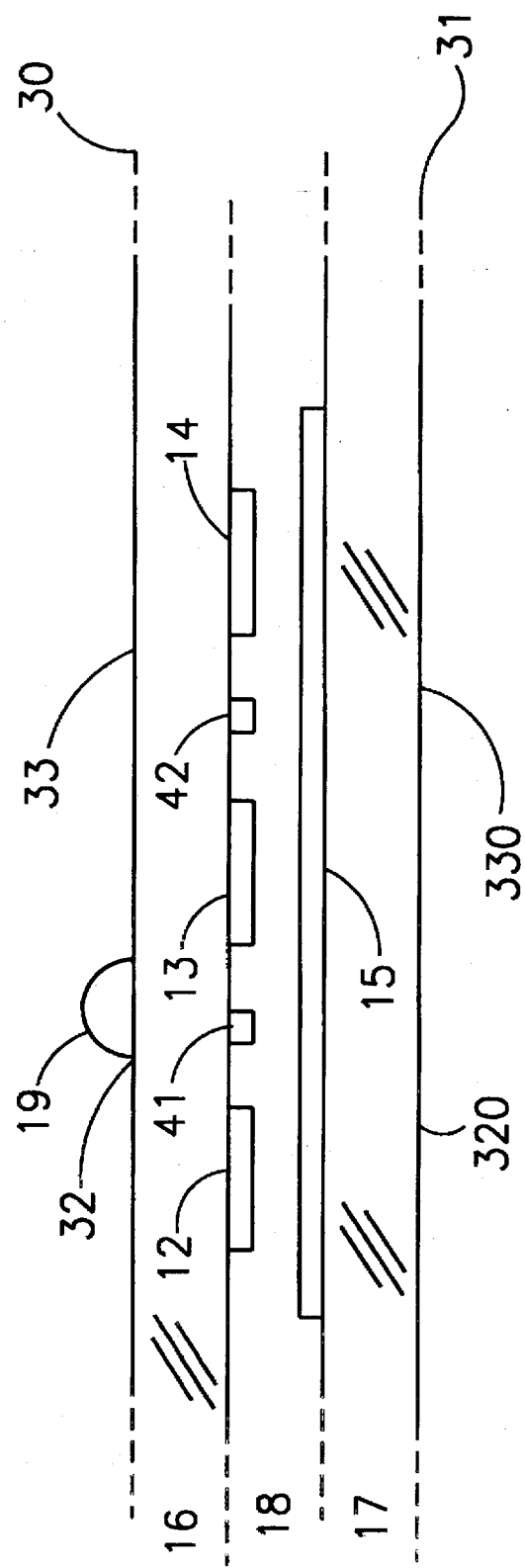
FIG. 3A is another modification of the sensor of FIG. 1A.
Figure 3B:
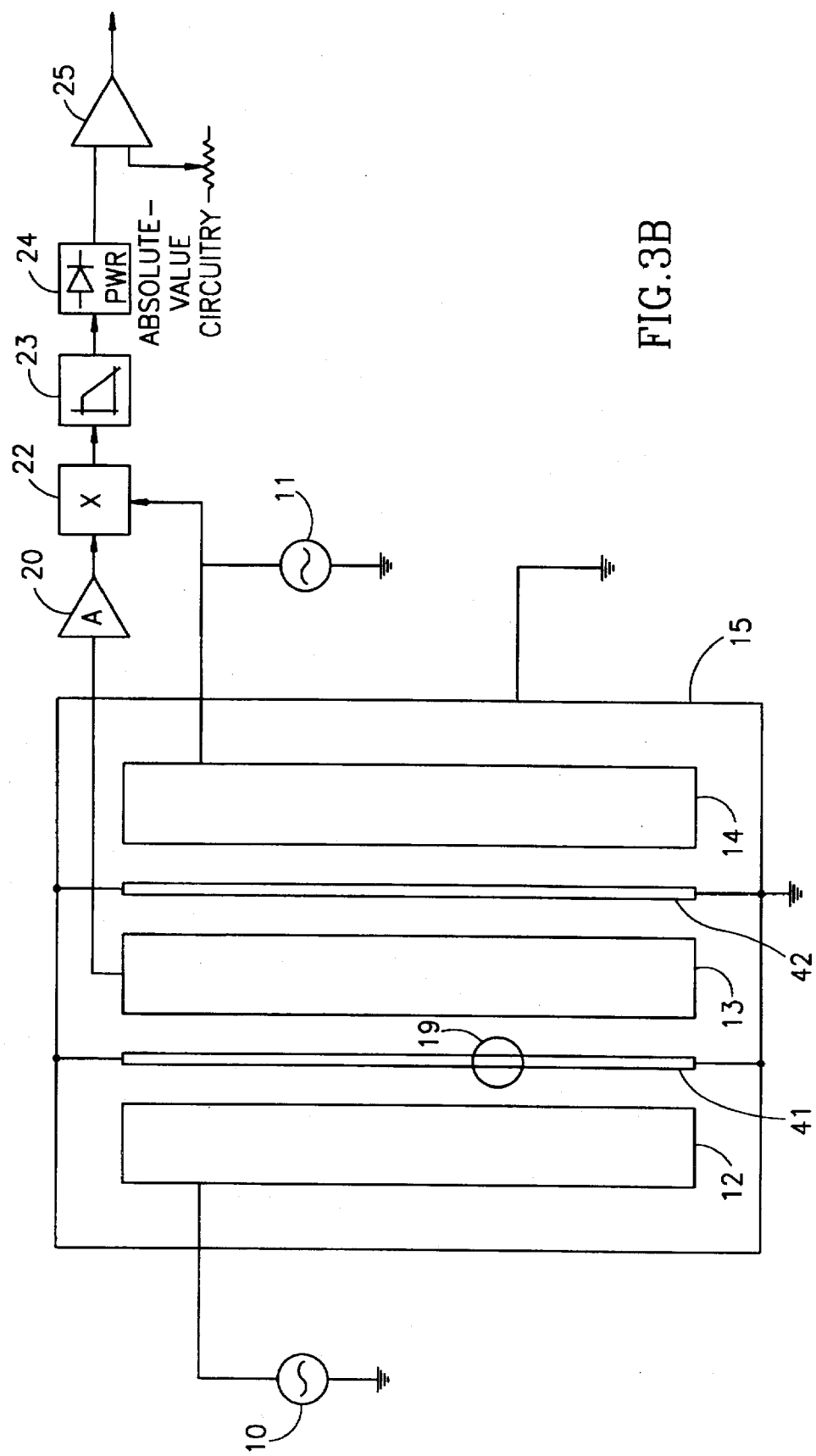
FIG. 3B is the sensor of FIG. 3A, with the electronics of FIG. 1A.

Yet another configuration is shown in FIGS. 3A and 3B. Here, a moisture sensor and electronics similar to that of FIGS. 1A and 1B, is modified by the addition of grounded shield electrodes, 41, and 42, between electrode pairs, 12 and 13, and 14 and 13, respectively, under sensing areas, 32 and 33, respectively. These shield electrodes reduce the coupling between the adjacent edges of the electrode pairs under the sensing areas, reducing the very-small non-moisture, "dry"-condition "offset" reference signal, hence, increasing the importance of the coupling via the sensing areas, 32 and 33, in providing a signal to sense electrode, 13. In practice, electrodes 41 and 42 should probably be a guard ring, surrounding electrode 13, and not two separate conductive strips. This guard ring may be "bootstrapped", i.e., driven from a voltage-follower output, whose input is connected to electrode, 13. This should be a more-effective capacitance-reduction technique than just grounding the guard ring. The shield electrode, 15, in FIGS. 3A and 3B, and in FIGS. 1A and 1B may also be bootstrapped. This bootstrapping would be useful if the transimpedance "charge" amplifier, 20, is replaced by a voltage amplifier, since then there would otherwise be capacitive division of the signal at sense electrode 13, concerning bootstrapping of electrode 15 in FIGS. 1A and 3A, refer to FIG. 1C. The electrical schematic shows nodes 112, 113, and 114 representing points of connection to active electrodes 12, 13, and 14 respectively, and 115, corresponding to connection to plate 15. There will be a parasitic capacitance from plate 13 and node 113, to plate 15 and node 115. This capacitance forms a voltage divider to plate 15 and node 115, which attenuates the input signal to amplifier 20, present on plate 13, node 113, if plate 15, node 115, is grounded. But if plate 15, node 115, is bootstrapped to plate 13, node 113, with a buffer amplifier (1115, FIG. 1D), then the voltage on nodes 113 and 115 is equal, and there is no capacitive divider action, so a larger signal, the maximum signal possible at node 113, will be provided to amplifier 20 by electrode 13.

Figure 6A:
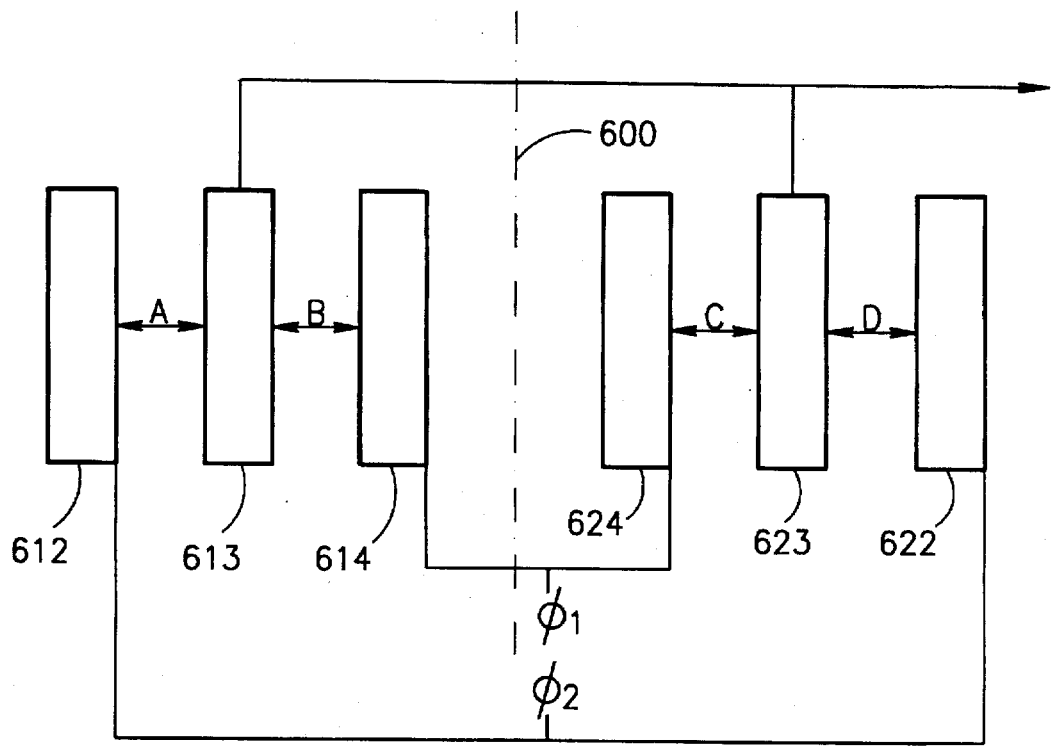
FIG. 6A is an interconnection of a pair of unit sensors of FIG. 1A in a beneficial manner.
Figure 6B:
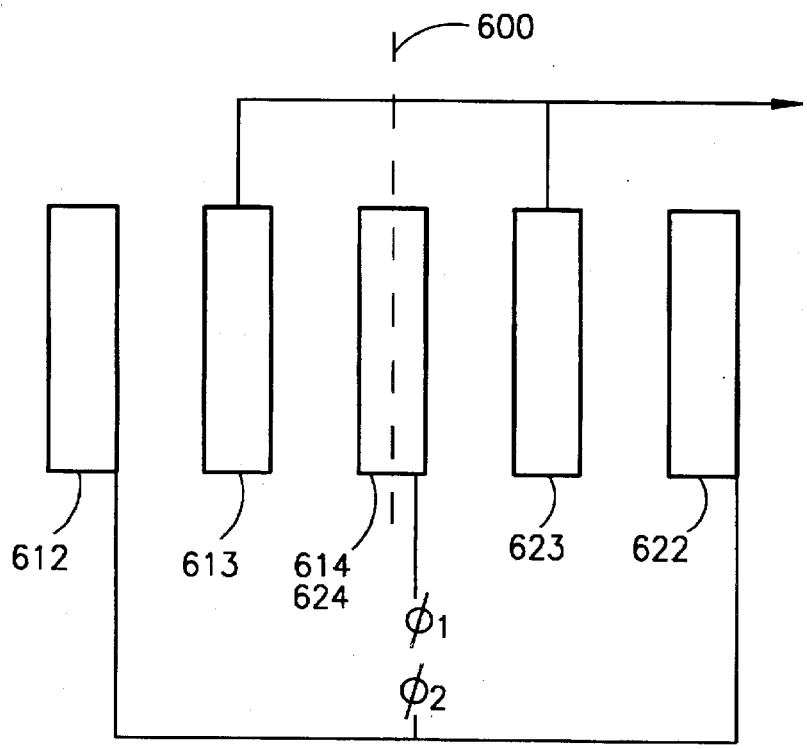
FIG. 6B is a simplification of FIG. 6A.

Yet another configuration is shown in FIG. 6A, and simplified in FIG. 6B. This composite sensor is the combination of two unit sensors of the type of FIG. 1A. In the unit sensor of FIG. 1A, if a stress applied to the substrate results in an expansion, for example, of the distances between electrode pairs 12 and 13, and 13 and 14, then the moisture-sensing sensitivities in regions 32 and 33, respectively, will change. If there is a uniform expansion, i.e., an equal increase in the two electrode-pair separations, then the sensor remains balanced, and no false output results. If, however, there is a gradient, a non-uniform expansion, so that the separation between one pair of plates is greater than that between the other pair, then a false output signal will result. The configuration of FIGS. 6A, 6B, solves this problem, by interconnecting two unit sensors, in such a way that the expansion gradient will be cancelled. With respect to FIG. 6A, electrodes 612 and 622 correspond to electrode 12 in FIG. 1A; electrodes 613 and 623 correspond to electrode 13 in FIG. 1A; electrodes 614 and 624 correspond to electrode 14 in FIG. 1A. Therefore the signal output due to moisture in the sensing regions between electrodes 612 and 613, and 622 and 623, add together, and the signal output due to moisture in the sensing regions between electrodes 613 and 614, and 623 and 624, add together. The difference between these added moisture-signal pairs provides the moisture-present indication as explained above. Now, if there would be a uniform expansion of the sensor, increasing all four spacings, labeled, a, b, c, d, the sensor remains balanced; and also, unique to this parallel interconnection of two unit sensors, in case of a gradient expansion increase of spacings, the sensor also remains balanced. This is easily seen as follows: assume a gradient expansion such that the distance increase at a is greater than at b, which is greater than at c, which is greater than at d. But the gradient is assumed to be uniform, so the distances (a+d)=(b+c), and the net combination sensor remains balanced when subjected to gradient stress. To achieve this, the two unit sensors must be symmetrically placed about a common center line, 600. Since electrodes 614 and 624 in FIG. 6A are adjacent, and bracket the outer line, 600, and are connected together, the two sensors of FIG. 6A may be made more compact by combining the two electrodes, 614, and 624, into one electrode as in FIG. 6B, in which the center line, 600, now bisects the one combined electrode. This illustrates one composite sensor with greater immunity to substrate lateral dimensional variations than one unit sensor alone. Similar argument also applies to a gradient thickness change.

Figure 7A:
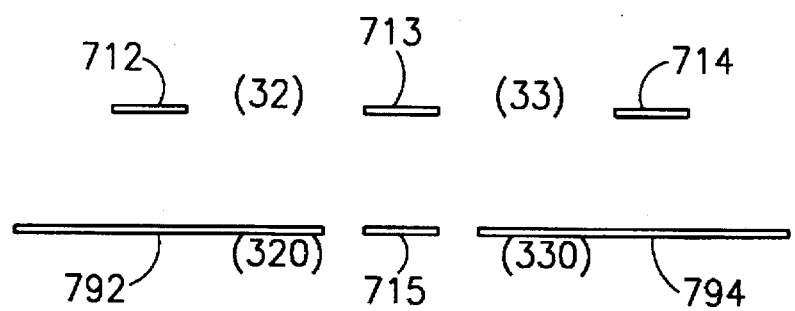
FIG. 7A is a modified sensor based on that of FIG. 2A.
Figure 7B:
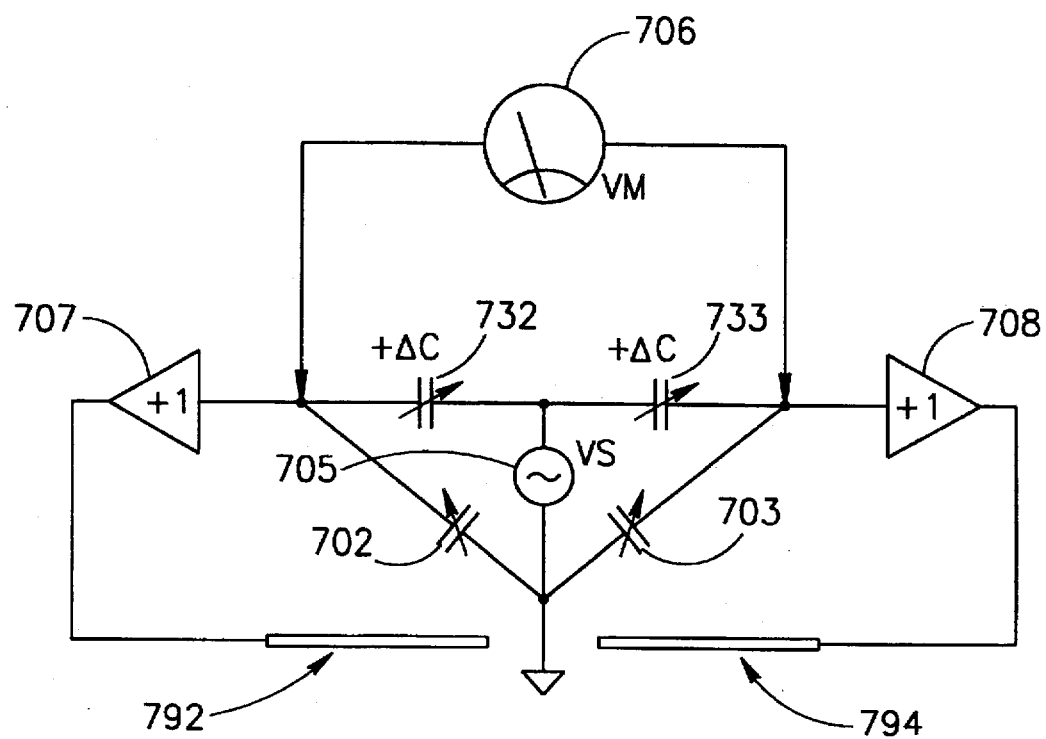
FIG. 7B is a circuit representation of the sensor of FIG. 7A.

Yet another configuration is shown in FIG. 7A, and an electrical circuit representation of it, in FIG. 7B. This is a modification of the sensor of FIG. 2A, in such a manner that the same gradient-dimensional-change problem solved above in FIG. 6A, 6B by a combination of two sensors, is solved in one sensor. In FIG. 7A, electrodes 712, 713, 714, and 715, correspond to electrodes 120, 130, 140, and 15 in FIG. 2A. In FIGS. 2A, 2B, electrode 15 is both the shield against sensing of moisture in regions 320 and 330, and also the electrical ground return for excitation source 36. The electrical equivalent circuit in FIG. 2C shows that two capacitors, 132, and 133 vary with moisture in regions 32 and 33, respectively. Capacitors, 232 and 233, from electrodes 120 to 15, and 140 to 15, respectively, serve as reference capacitors for the capacitor bridge circuit, and do not change value with moisture. This sensor has the same dimensional-change properties as the sensor of FIG. 1A.

Now in the sensor of FIG. 7A, electrode 715 has been reduced in the width to correspond approximately to the width of electrode 713. Electrode 715, therefore, will be affective as the electrical return node for the bridge, and the capacitances, 702 and 703, in FIG. 7B will be reduced compared with capacitances, 232 and 233, in FIG. 2C. But, capacitance 702 will vary with dimensional changes in the same manner as capacitor 732, and capacitor 703 will vary with dimensional changes in the same manner as capacitor 733, so the reference capacitance corresponding to each sensor capacitance varies with stress proportionally, and the bridge remains balanced for gradient dimensional changes, as well as for uniform dimensional changes. Thus the sensor of FIG. 7A is an improvement in this respect.

The problem of providing directionality is solved by adding shield electrodes, 792, and 794, below sensing electrodes, 712, and 714, respectively, and bootstrapping them with unity-gain amplifiers, 707, and 708, respectively, to restore effective shielding against moisture in regions 320 and 330. The shield electrode, 15, of FIGS. 2A, 2B, has thus been replaced by a multiple-section shield, or multiple shields, segments, portions of which, are either grounded or bootstrapped to their corresponding sensing electrodes, as appropriate to the sensor design.

Yet another configuration results from just modifying dimensions of the sensor active electrodes to take into account the physical limitations of the specific manufacturing process used, for example, in the case of lamination in an automobile windshield, as has been discussed. Ideally, a combination of a perfect windshield and a uniform layer of moisture would result in zero output signal. When used as a windshield fog sensor, a situation may occur, that the fog is sufficiently uniform as to create a very small signal. In other words, for the sensor to respond to a uniform moisture layer, the sensor should not be perfectly balanced. This required imbalance may be implemented either mechanically or electronically. In practice, the windshield laminates thicknesses are not perfectly uniform. Therefore, the distance between the moisture layer and the electrode plane is not fixed, and the capacitively induced currents do not cancel, even with a uniform layer of moisture. Thus, in a realistic sensor, a signal will be generated even when the moisture layer is perfectly uniform. On the other hand, such a sensor also responds to common mode effects such as heating of the windshield, but in practice, it has been found that there is no contradiction; and the amount of nonuniformity in practical windshields is sufficiently small to eliminate false signals due to temperature and mechanical stresses, yet sufficiently large to sense even a uniform layer of fog.

In a preferred embodiment of the invention, the sensor is deliberately made slightly asymmetrical, for example, by making the lengths of the opposing excitation electrode slightly different, to ensure that even when the laminates happen to be uniform in thickness, a uniform moisture layer could be sensed. This method applies to any of the sensors of the present invention, as it is inherent in the structure.

Figure 8:
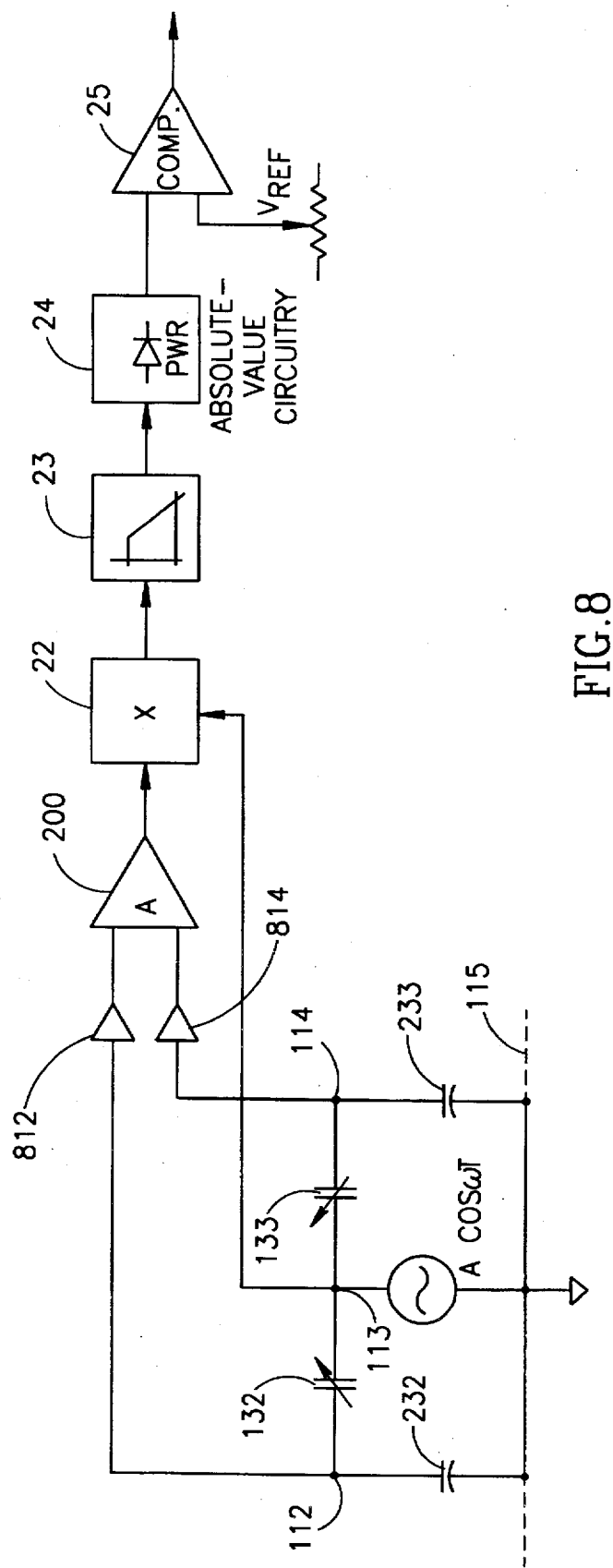
FIG. 8 is as FIG. 2c but with the inclusion of a pair of amplifiers.

Asymmetry of output in the case of a mechanically perfectly-balanced sensor may also be provided electronically, as mentioned above. This method applies in the case of sensors of the types shown in FIGS. 2A, 2B, and FIGS. 7A, and shown schematically in FIGS. 2C, and 7B, respectively. These sensors are "bridge" sensors, in which the output is taken differentially between two output nodes. The electronic imbalance is provided simply by providing different electronic gains to the signals available at the two bridge output nodes, for example with separate preamplifiers 812 and 814 (FIG. 8), and applying the outputs of these preamplifiers to the differential amplifier that would otherwise have been directly connected to the two bridge output nodes.

Figure 9A:
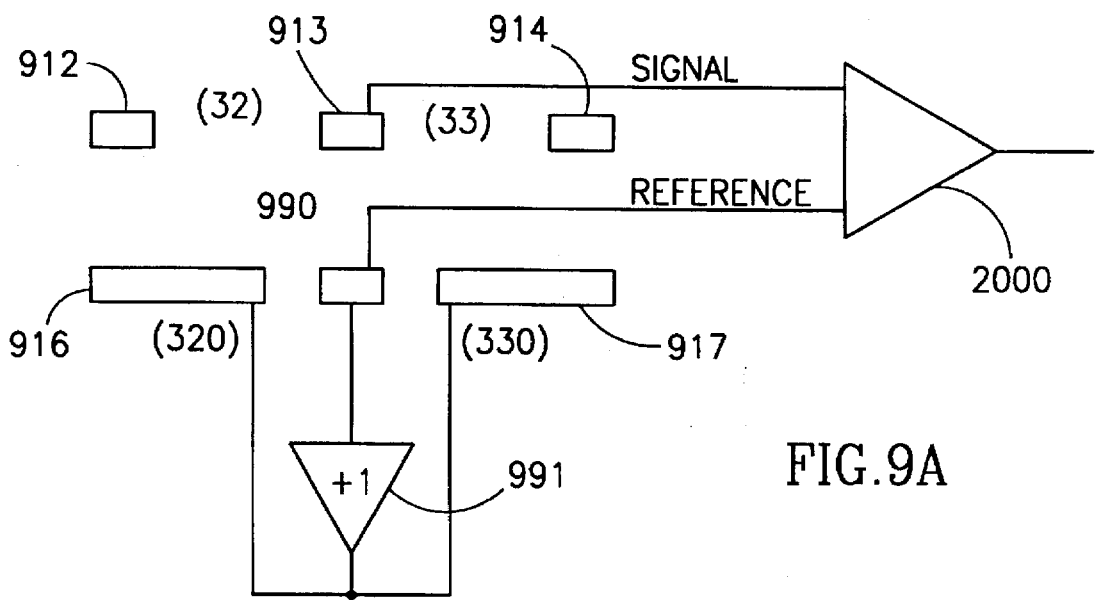
FIG. 9A is a modified sensor based on that of FIG. 1A.
Figure 9B:
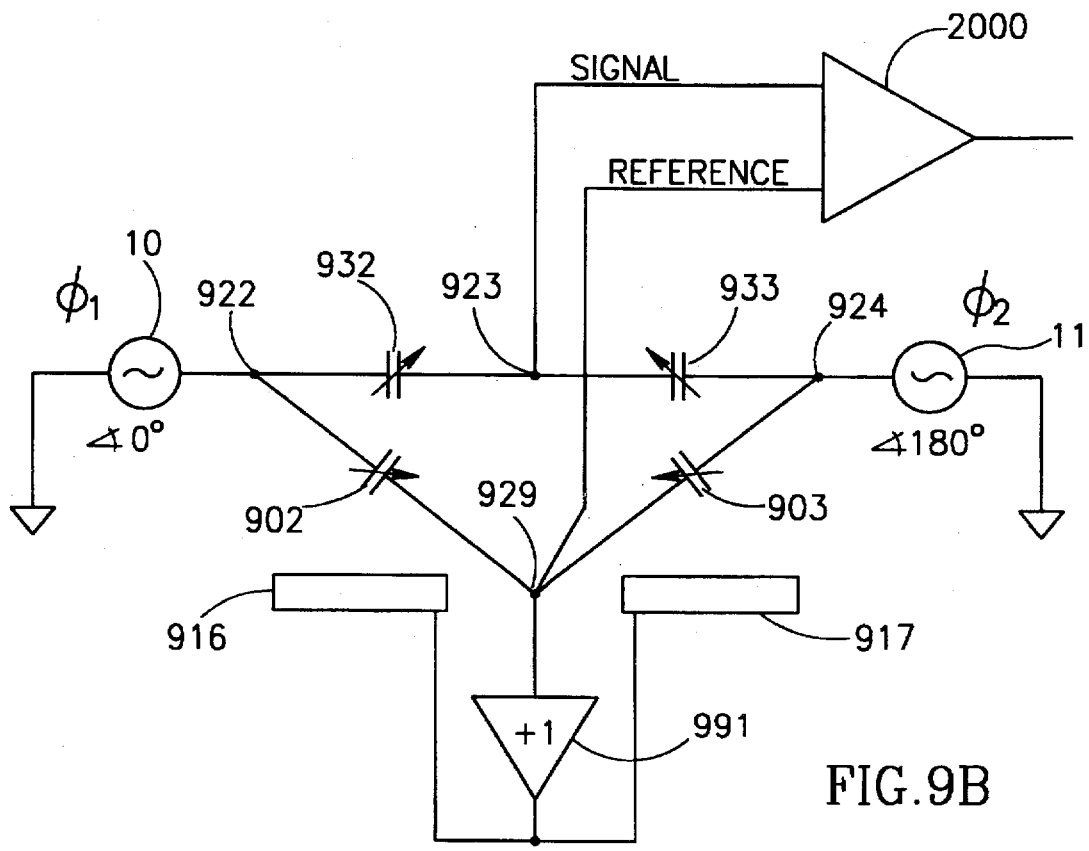
FIG. 9B is an electrical representation of the sensor of FIG. 9A.

Yet another configuration is shown in FIGS. 9A and 9B. Here, electrodes 912 and 914 are driven by balanced, 180-degree out-of-phase sources 10 and 11, and the signal output is taken at electrode 913, as in the FIG. 1A, etc., sensor. This version of the sensor includes an active electrode, 990, below electrode 913. Electrode 990 receives a "dry" reference signal depending on a capacitive-divider effect between capacitors 902 and 903, whose values will also be dimensionally-dependent, substantially similarly to capacitors 932 and 933, which are the capacitive couplings via the moisture-sensing regions 32 and 33, respectively. An amplifier with inputs connected to electrodes 913 and 990, nodes 923 and 929, respectively, will develop a moisture-dependant output signal; but, since both lateral capacitive dividers will have similar substrate-dimensional variation "dry" capacitance sensitivities, the sensor output will be substantially independent of substrate-dimensional variation. The addition of shield electrodes 916 and 917, below electrodes 916 and 917, respectively, and bootstrap amplifier, 991, bootstrapping electrodes 916 and 917 to active reference electrode 990, node 929, provides sensor directionality. Without electrodes 916 and 917, and bootstrap amplifier 991, as above, the sensor could be used to differentially sense moisture on an upper moisture-sensitive surface versus moisture on a lower moisture-sensitive surface, but this is not the goal in the automotive windshield application.

The relative dimensions of the electrodes 916, 917, and 990, may be adjusted to minimize the actual substrate dimensional sensitivity. If a charge amplifier is used, then the reference output will be its reference, rather than system signal ground. Alternatively, a differential voltage amplifier may be used.

While the invention has been described with respect to a limited number of embodiments, it will be appreciated that many variations, modifications, and other applications of the invention may be made.

For example, the moisture detector of the invention may be implemented as a stand-alone device, not integrally simultaneously fabricated with the automotive windshield, but which can be mounted to an existing windshield. In this case, it is not necessary to use the laminated "sandwich" glass substrate, but deposition of electrodes on the two sides of a flexible plastic sheet substrate would be sufficient, in which case this device would then be adhered onto the windshield, and wires would connect to the electronics package. A sandwich glass-substrate could also be made, but would usually require glass substrate with matching curvature to that of the windshield it was to be mounted on.

Additionally, further benefit may result from interconnection of a multiplicity of moisture sensors which sense regions of the same surface, to provide a resulting overall moisture sensor which is still less sensitive to substrate changes than one sensor alone.

What is claimed is:

1. A differential capacitive moisture sensor having first and second surfaces for sensing moisture on the first surface of the moisture sensor, comprising at least three non-reference active electrodes located in an electrode plane parallel to, and between the planes of said first and second surfaces, defining two sensing regions on the first surface of the sensor, whereby a differential output signal is developed, which depends on the difference between the amounts of moisture in said two sensing regions, thereby enabling detection of the presence of moisture on said first surface.

2. The sensor of claim 1, wherein said non-reference active electrodes are substantially co-planar with each other and parallel to the surface having said sensing regions.

3. The sensor of claim 1, further comprising a temperature sensor for sensing temperature of the surface.

4. A composite sensor comprising at least a first and a second sensor, each of said sensors being as in claim 1, with non-reference active electrodes interconnected in such a manner that the signal outputs are added together to cancel the effect of substrate dimensional variations.

5. The sensor of claim 1, wherein said non-reference active electrodes are fabricated by vacuum deposition of a transparent conductive metal thin film on a substrate.

6. The sensor of claim 5, further comprising a temperature sensor fabricated by vacuum deposition of said transparent conductive metal thin film on said substrate.

7. The sensor of claim 5, further comprising a temperature sensor fabricated by vacuum deposition of a second transparent thin film on said substrate.

8. The sensor of claim 1, further comprising guard electrodes bracketing said non-reference active electrodes.

9. The sensor of claim 8, wherein each of said guard electrodes is bootstrapped to each of its corresponding said non-reference active electrodes.

10. The sensor of claim 1, further comprising at least one guard electrode between two of said non-reference active electrodes.

11. The sensor of claim 10, further comprising a center sensing electrode to which said guard electrodes are bootstrapped.

12. The sensor of claim 1, further comprising a shield electrode, said shield electrode serving to reduce sensitivity to moisture on the second surface of the moisture sensor.

13. The directional sensor of claim 12, further comprising a temperature sensor.

14. The directional sensor of claim 12, further comprising a simultaneously fabricated heating element.

15. The sensor of claim 12, wherein said shield electrode is substantially parallel to the plane of said non-reference active electrodes.

16. The directional sensor of claim 15, wherein said sensor is structured as a laminated assembly, including,
   (a) a first glass laminate, having two substantially parallel surfaces, with a first surface containing said sensing regions;
   (b) a plastic laminate, having two substantially parallel surfaces, with a first surface of said plastic laminate adjacent to a second surface of said first glass laminate;
   (c) said non-reference active electrodes located on said first surface of said plastic laminate;
   (d) a second glass laminate, having two substantially parallel surfaces;
   (e) a shield electrode on a second surface of said plastic laminate; and,
   (f) a first surface of said second glass laminate adjacent to said second surface of said plastic laminate.

17. The directional sensor of claim 15, wherein said sensor is structured as a laminated assembly, including,
   (a) a first glass laminate, having two substantially parallel surfaces, with a first surface containing said sensing regions;
   (b) said non-reference active electrodes located on the second surface of said first glass laminate;
   (c) a plastic laminate, having two substantially parallel surfaces, with a first surface of said plastic laminate adjacent to said second surface of said first glass laminate;
   (d) a second glass laminate, having two substantially parallel surfaces;
   (e) a shield electrode on a first surface of said second glass laminate; and,
   (f) said first surface of said second glass laminate adjacent to a second surface of said plastic laminate.

18. The sensor of claim 17, further comprising at least one temperature sensor fabricated on at least one electrode bearing surface of said glass laminates.

19. The sensor of claim 15, wherein said shield electrode and said non-reference active electrodes are located on two opposite surfaces of a standalone substrate.

20. The directional sensor of claim 19, further comprising a temperature sensor.

21. A sensor as in claim 19, further comprising said standalone substrate laminated inside a glass windshield.

22. A sensor as in claim 19, further comprising said standalone substrate mounted on a surface of a windshield.

23. The sensor of claim 1, further comprising a shield electrode located below a center active electrode, said shield electrode serving as a ground return for an excitation applied to said center non-reference active electrode.

24. The sensor of claim 23, further comprising additional shield electrodes below their corresponding non-reference active electrodes, said non-reference active electrodes serving as sense electrodes, said shield electrodes extending under their adjacent sensing areas, said shield electrodes bootstrapped to their corresponding sense electrodes.

25. The sensor of claim 23, further comprising non-reference active electrodes, serving as sense electrodes, wherein said sense electrodes, and said center non-reference active electrode are designed to provide a mechanically asymmetrical sensor.

26. The sensor of claim 1, further comprising a reference electrode located below a center non-reference active electrode, said reference electrode serving as a reference for a sensor output signal at said center non-reference active electrode.

27. The sensor of claim 26, further comprising shield electrodes bootstrapped to said reference electrode.

28. A method for sensing moisture on a surface, comprising the steps of:
   a) providing a differential capacitive moisture sensor having first and second surfaces for sensing moisture on the first surface of the moisture sensor, comprising at least three non-reference active electrodes located in an electrode plane parallel to, and between the planes of said first and second surfaces, defining two sensing regions on the first surface of the sensor, whereby a differential output signal is developed, which depends on the difference between the amounts of moisture in said two sensing regions, thereby enabling detection of the presence of moisture on said first surface;

b) applying excitation to one or more of said electrodes;

c) measuring signal output at one or more of said electrodes.

29. The method of claim 28, further comprising absolute value circuitry for detecting imbalance of either polarity.

30. The method of claim 28, further comprising providing asymmetrical electrodes.

31. The method of claim 28, wherein:

a center electrode serves as a sensing electrode;

b) balanced 180-degree out-of-phase excitations are applied to two of the remaining electrodes.

32. The method of claim 31, further comprising providing a grounded shield electrode below said non-reference active electrodes.

33. The method of claim 31, further comprising providing a shield electrode below said non-reference active electrodes, said shield electrode being bootstrapped to said center electrode.

34. The method of claim 31, further comprising providing a reference electrode below said sensing electrode.

35. The method of claim 28, wherein excitation is applied to a center non-reference active electrode, wherein a grounded shield electrode in a plane parallel to, and between, said electrode plane and said second surface serves as the ground return for said excitation, and said signal output is measured differentially between two of said non-reference active electrodes which serve as sense electrodes.

36. The method of claim 35, wherein said grounded shield electrode includes the area and dimensions of the projection of said sense electrodes on the plane of said shield electrode, thereby providing directionality.

37. The method of claim 35, wherein said grounded shield electrode is substantially of the dimensions of said center excitation electrode and wherein an additional shield electrode is provided below each said sense electrode, each said shield electrode bootstrapped to said sense electrode corresponding to each said shield electrode, and each said shield electrode extending close to said grounded shield electrode below said center excitation electrode.

38. The method of claim 35, further comprising providing preamplifiers of different gains connected to said non-reference active electrodes which serve as sense electrodes.

39. A differential capacitive moisture sensor assembly for sensing moisture on two substantially parallel surfaces, comprising at least a first and second directional sensors, each of said directional sensors including:

(a) at least three non-reference active electrodes.

(b) a shield electrode, said shield electrode serving to provide directionality, said shield electrode being substantially parallel to the plane of said non-reference active electrodes;

each of said sensors being structured as a laminated assembly, including, (a) a first glass laminate, having two substantially parallel surfaces, with a first surface containing said sensing regions;

(b) said non-reference active electrodes located on the second surface of said first glass laminate;

(c) a plastic laminate, having two substantially parallel surfaces, with a first surface of said plastic laminate adjacent to said second surface of said first glass laminate;

(d) a second glass laminate, having two substantially parallel surfaces;

(e) a shield electrode on a first surface of said second glass laminate; and, (f) said first surface of said second glass laminate adjacent to a second surface of said plastic laminate; and, wherein said first glass laminate of said first sensor serving as said second glass laminate of said first sensor.

40. A differential capacitive moisture sensor assembly for sensing moisture on two substantially parallel surfaces, comprising at least a first and second directional sensors, each of said directional sensors including:

(a) at least three non-reference active electrodes, (b) a shield electrode, said shield electrode serving to provide directionality, said shield electrode being substantially parallel to the plane of said non-reference active electrodes;

each of said sensors being structured as a laminated assembly, including, (a) a first glass laminate, having two substantially parallel surfaces, with a first surface containing said sensing regions;

(b) a plastic laminate, having two substantially parallel surfaces, with a first surface of said plastic laminate adjacent to a second surface of said first glass laminate;

(c) said non-reference active electrodes located on said first surface of said plastic laminate;

(d) a second glass laminate, having two substantially parallel surfaces;

(e) a shield electrode on a second surface of said plastic laminate; and, (f) a first surface of said second glass laminate adjacent to said second surface of said plastic laminate; and, wherein said first glass laminate of said first sensor serving as said second glass laminate of said first sensor.

* * * * *